US009523865B2

(12) United States Patent
Pletcher et al.

(10) Patent No.: US 9,523,865 B2
(45) Date of Patent: Dec. 20, 2016

(54) CONTACT LENSES WITH HYBRID POWER SOURCES

(75) Inventors: Nathan Pletcher, Mountain View, CA (US); Brian Otis, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 291 days.

(21) Appl. No.: 13/559,261

(22) Filed: Jul. 26, 2012

(65) Prior Publication Data

US 2014/0192311 A1 Jul. 10, 2014

(51) Int. Cl.
*G02B 7/04* (2006.01)
*G02C 7/04* (2006.01)
*A61B 5/145* (2006.01)
*A61B 5/00* (2006.01)

(52) U.S. Cl.
CPC ............. *G02C 7/04* (2013.01); *A61B 5/14507* (2013.01); *A61B 5/14532* (2013.01); *A61B 5/6821* (2013.01)

(58) Field of Classification Search
CPC ....................................................... G02C 7/04
USPC .......................... 351/159.02, 159.03, 159.73
See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |

(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

(Continued)

*Primary Examiner* — Darryl J Collins
(74) *Attorney, Agent, or Firm* — McDonnell Boehnen Hulbert & Berghoff LLP

(57) ABSTRACT

Apparatus, systems and methods of contact lenses with power sources are provided. In some aspects, a contact lens can include a substrate; and a circuit. The circuit can include: one or more sensors disposed on or within the substrate; circuitry disposed on at least a portion of the substrate; one or more photovoltaic cells disposed on at least a portion of the substrate; and a hybrid power component that supplies at least one of two or more different types of power to the circuitry, wherein at least one of the two or more different types of power is radio frequency/inductive power. In various aspects, other types of power can be solar and/or microelectromechanical system power. Additionally, in various aspects, photovoltaic cells can be arrayed in different configurations and/or over a significant portion of a viewing surface of the contact lens. In some aspects, the photovoltaic cells can be transparent.

33 Claims, 8 Drawing Sheets

(56) References Cited

U.S. PATENT DOCUMENTS

| | | |
|---|---|---|
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 9,133,024 B2 * | 9/2015 | Phan .................. B01L 3/50273 |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1* | 6/2004 | Fink et al. ..................... 600/398 |
| 2004/0242976 A1* | 12/2004 | Abreu ........................... 600/315 |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0076974 A1* | 3/2008 | Yamazaki et al. ............ 600/300 |
| 2008/0091090 A1* | 4/2008 | Guillory et al. .............. 600/301 |
| 2008/0139953 A1* | 6/2008 | Baker et al. .................. 600/509 |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0191072 A1* | 7/2010 | Matsumori et al. .......... 600/301 |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0068848 A1* | 3/2012 | Campbell et al. .......... 340/573.1 |
| 2012/0069254 A1 | 3/2012 | Burton |
| 2012/0075168 A1 | 3/2012 | Osterhout et al. |
| 2012/0075574 A1 | 3/2012 | Pugh et al. |

(56) References Cited

U.S. PATENT DOCUMENTS

| | | | |
|---|---|---|---|
| 2012/0078071 | A1 | 3/2012 | Bohm et al. |
| 2012/0088258 | A1 | 4/2012 | Bishop et al. |
| 2012/0092612 | A1 | 4/2012 | Binder |
| 2012/0109296 | A1 | 5/2012 | Fan |
| 2012/0177576 | A1 | 7/2012 | Hu |
| 2012/0201755 | A1 | 8/2012 | Rozakis et al. |
| 2012/0245444 | A1 | 9/2012 | Otis et al. |
| 2012/0259188 | A1 | 10/2012 | Besling |
| 2012/0271121 | A1* | 10/2012 | Della Torre et al. ......... 600/301 |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

"Contact Lenses: Look Into My Eyes," The Economist, Jun. 2, 2011, http://www.economist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Ho et al., "Contact Lens With Integrated Inorganic Semiconductor Devices," MEMS 2008. IEEE 21st International Conference on. IEEE, 2008., pp. 403-406.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Murdan, "Electro-responsive drug delivery from hydrogels," Journal of Controlled Release, 2003, pp. 1-17, vol. 92.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Singh, et al., "Novel Approaches in Formulation and Drug Delivery using Contact Lenses," Journal of Basic and Clinical Pharmacy, May 2011, pp. 87-101, vol. 2, Issue 2.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Bionic contact lens 'to project emails before eyes,' http://www.kurzweilai.net/forums/topic/bionic-contact-lens-to-project-emails-before-eyes, Last accessed Mar. 14, 2012, 2 pages.

Tweedie, et al., "Contact creep compliance of viscoelastic materials via nanoindentation," J. Mater. Res., Jun. 2006, vol. 21, No. 2, pp. 1576-1589, Materials Research Society.

Brahim, et al., "Polypyrrole-hydrogel composites for the construction of clinically important biosensors," 2002, Biosensors & Bioelectronics, vol. 17, pp. 53-59.

Huang, et al., "Wrinkling of Ultrathin Polymer Films," Mater. Res. Soc. Symp. Proc., 2006, vol. 924, 6 pages, Materials Research Society.

Zarbin, et al., "Nanotechnology in ophthalmology," Can J Ophthalmol, 2010, vol. 45, No. 5, pp. 457-476.

Selner, et al., "Novel Contact Lens Electrode Array for Multi-electrode Electroretinography (meERG)," IEEE, 2011, 2 pages.

Liao, et al., "A 3-μW CMOS Glucose Sensor for Wireless Contact-Lens Tear Glucose Monitoring," IEEE Journal of Solid-State Circuits, Jan. 2012, vol. 47, No. 1, pp. 335-344.

Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.

Thomas, et al., "Functional Contact Lenses for Remote Health Monitoring in Developing Countries," IEEE Global Humanitarian Technology Conference, 2011, pp. 212-217, IEEE Computer Society.

(56) References Cited

OTHER PUBLICATIONS

Pandey, et al., "A Fully Integrated RF-Powered Contact Lens With a Single Element Display," IEEE Transactions on Biomedical Circuits and Systems, Dec. 2010, vol. 4, No. 6, pages.

Lingley, et al., "Multipurpose integrated active contact lenses," SPIE, 2009, 2 pages.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.

Liao, et al., "A 3 µW Wirelessly Powered CMOS Glucose Sensor for an Active Contact Lens," 2011 IEEE International Solid-State Circuits Conference, Session 2, Feb. 21, 2011, 3 pages.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Lončar, et al., "Design and Fabrication of Silicon Photonic Crystal Optical Waveguides," Journal of Lightwave Technology, Oct. 2000, vol. 18, No. 10, pp. 1402-1411.

Liu, et al., "Miniature Amperometric Self-Powered Continuous Glucose Sensor with Linear Response," Analytical Chemistry, 7 pages, Mar. 14, 2012.

Baxter, "Capacitive Sensors," 2000, 17 pages.

Lingley, et al., "A Single-Pixel Wireless Contact Lens Display," Journal of Micromechanics and Microengineering, 2011, 9 pages.

International Searching Authority, International Search Report and Written Opinion for International Application No. PCT/US2014/024124 mailed Dec. 16, 2014, 17 pages.

\* cited by examiner

CONTACT LENSES WITH HYBRID POWER SOURCES

TECHNICAL FIELD

This disclosure generally relates to contact lenses having hybrid power sources.

DETAILED DESCRIPTION

Figure 1:
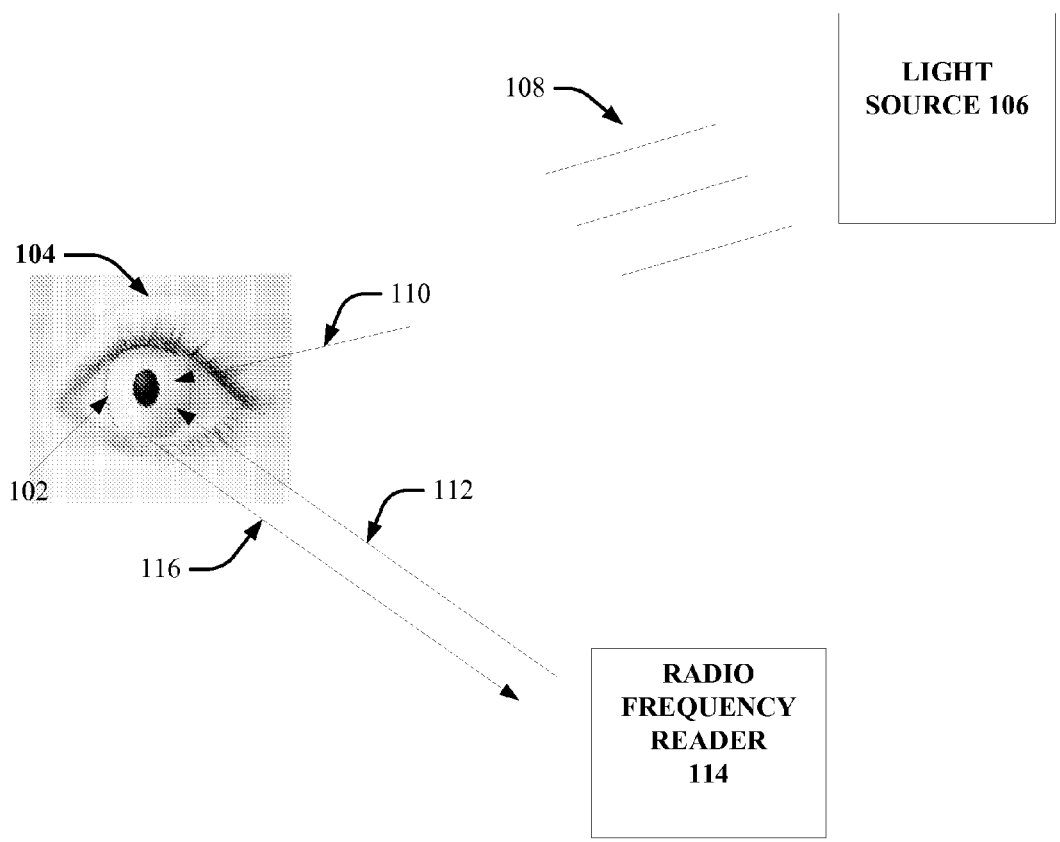
FIG. 1 is an illustration of a block diagram of an exemplary non-limiting system that facilitates contact lenses having hybrid power sources in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects.

Apparatus, systems and/or methods disclosed herein relate to contact lenses having hybrid power sources. In particular, in one aspect, a contact lens can include: a substrate; and a circuit. The circuit can include: one or more sensors disposed on or within the substrate; circuitry disposed on or within at least a portion of the substrate; one or more photovoltaic cells disposed on or within at least a portion of the substrate; and a hybrid power component that supplies at least one of two or more different types of power to the circuitry, wherein at least one of the two or more different types of power is RF/inductive power.

In another aspect, a contact lens can include: a substrate; and a circuit. The circuit can include: one or more sensors disposed on or within the substrate; circuitry disposed on or within at least a portion of the substrate; and one or more solar cells disposed on or within at least a portion of the substrate, that supply power to the circuitry, wherein the one or more solar cells are transparent.

In another aspect, a method can include: supplying, from a hybrid power component on or within the contact lens, at least one of two or more different types of power to circuitry disposed on or within the contact lens, wherein at least one of the two or more different types of power is RF/inductive power; and performing one or more operations, by the circuitry, in response to receiving the supplied power.

In another aspect, a method can include: determining at least one of a type of operation performed via the contact lens or an environment outside of the contact lens; selecting a type of power based, at least, on the type of the operation or the environment outside of the contact lens; and outputting the type of the power.

One or more aspects of the apparatus, systems and/or methods described herein can advantageously facilitate two or more different forms of power supply on contact lenses. In various aspects, the different forms of power can be supplied intermittently, periodically, based on conditions and the like.

FIG. 1 is an illustration of a block diagram of an exemplary non-limiting system that facilitates contact lenses having hybrid power sources in accordance with aspects described herein.

The system 100 can include a light source 106 that emits light rays 108 (resulting in light 110 incident on the contact lens 102), an RF reader 114 that emits RF energy 112, a contact lens 102 positioned on an eye 104 of a wearer of the contact lens and having a circuit (not shown). The circuit can include one or more sensors (not shown), a hybrid power component (not shown), photovoltaic or solar cells (not shown) and/or circuitry (not shown), disposed on or within a substrate of the contact lens 102.

The hybrid power component can supply different types of power in connection with the contact lens 102. For example, as described in greater detail with reference to FIG. 3, the hybrid power component can select a type of power to output from the hybrid power component. The power output can be supplied to the circuit, one or more sensors and/or any other portions of the contact lens 102 that employ power. In various aspects, the different types of power that the hybrid power component can output can include, but are not limited to, RF/inductive power, solar power and/or microelectrical mechanical systems (MEMS)-generated electric power.

In various aspects, the RF/inductive power can be received from an RF reader in the geographic proximity of the contact lens 102. For example, the RF/inductive power can be received via an antenna on the contact lens 102. In some aspects, the solar power can be received from sunlight and/or ambient light incident on photovoltaic cells of the contact lens 102. In some aspects, the MEMS-based power can be generated based, at least, on one or more MEMS devices on the contact lens 102. The MEMS devices can be adapted to generate power based, at least, on for example stress and corresponding deformation applied to the contact lens 102 when the wearer of the contact lens 102 blinks and the eyelid applies pressure to the contact lens 102 while the eyelid is closed.

In various aspects, the contact lens 102 can output information 116 to the RF reader 114 in response to detecting that the RF reader 114 is within a selected geographic proximity to the contact lens 102. For example, in some aspects, the contact lens 102 can include values or information sensed by the one or more sensors.

In some aspects, the system 100 includes the contact lens 102 having the circuit that includes one or more sensors, one or more photovoltaic or solar cells, the microelectromechanical system (MEMS) components, RF components (e.g., antenna), a power storage and/or circuitry disposed on or within a substrate of the contact lens.

Figure 2A:
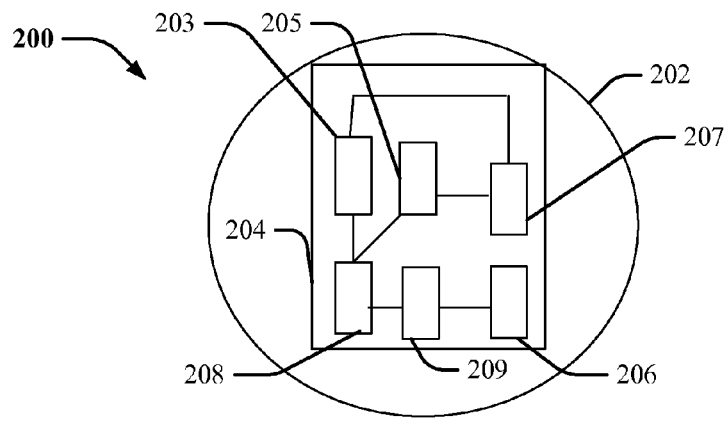
FIGS. 2A, 2B and 2C are illustrations of block diagrams of exemplary non-limiting contact lenses having hybrid power sources in accordance with aspects described herein.
Figure 2B:
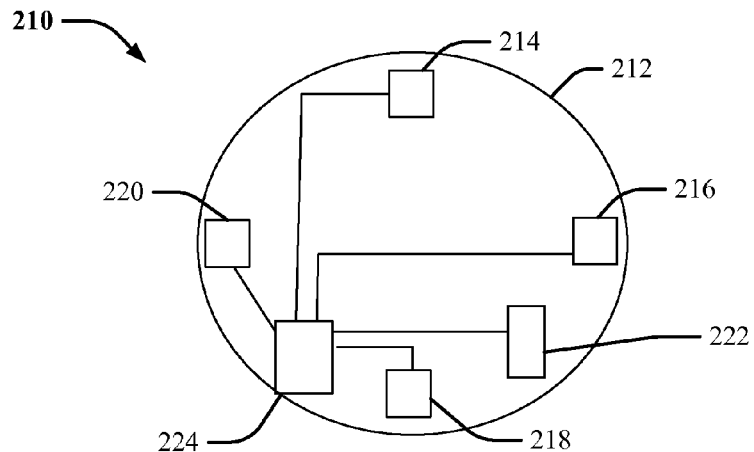
Figure 2C:
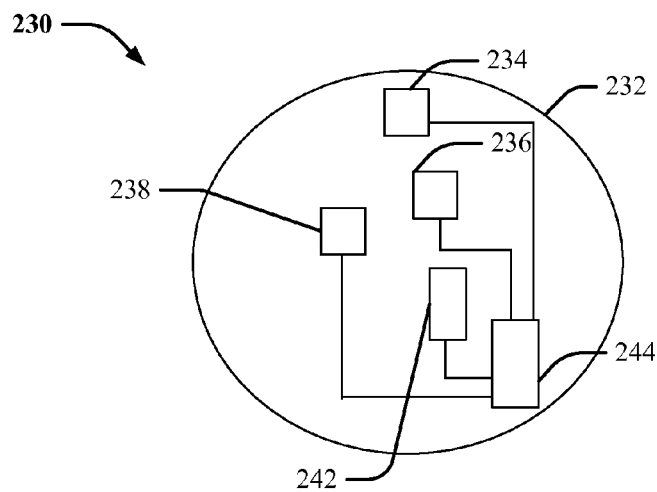

Various aspects of the contact lens will be described with reference to FIGS. 2A, 2B, 2C and 3. FIGS. 2A, 2B and 2C are illustrations of block diagrams of exemplary non-limiting contact lenses having hybrid power sources in accordance with aspects described herein.

Turning first to FIG. 2A, the contact lens 200 can include a substrate 202. In some aspects, the substrate 202 is formed to cover at least a portion of an iris of an eye. While not shown in FIG. 2A, in some aspects, the substrate 202 is formed as a ring. In various aspects, one or more portions of the substrate 202 can be transparent or translucent. In some aspects, the substrate 202 can be flexible or semi-rigid.

The contact lens 200 can include a circuit 204 disposed on or within the substrate 202. For example, in some aspects, the circuit 204 can be encapsulated in the substrate 202. In various aspects, the circuit 204 can include a number of chips, photovoltaic or solar cells and/or sensors communicatively and/or electrically coupled to one another and having one or more different functions. The photovoltaic cells can be single crystal silicon photovoltaic cells in some embodiments. In various embodiments, the photovoltaic cells can be formed from or include biocompatible organic dyes, thin films, organic polymers and/or nanocrystals in various aspects. The nanocrystals can be based on silicon, cadmium telluride or copper indium gallium (di)selenide. The organic polymers can be or include polyphenylene vinylene or copper phthalocyanine.

As shown in FIG. 2A, in some aspects, the circuit 204 can include one or more photovoltaic cells 203, 205, a sensor 206, a power storage component 207, a hybrid power component 208, and/or circuitry 209. In various aspects, the one or more photovoltaic cells 203, 205, sensor 206, power storage component 207, hybrid power component 208 and/or circuitry 209 can be operably, electrically and/or communicatively coupled to one another to perform one or more functions performed on or via the contact lens 200. One or more of the photovoltaic cells 203, 205, sensor 206, power storage component 207, hybrid power component 208 and/or circuitry 209 can be disposed on or within the substrate 202.

In some aspects, the sensor 206 can sense information associated with the wearer of the contact lens 200 (or information associated with an environment outside of the contact lens). Accordingly, in various aspects, the sensor 206 can sense biological and/or chemical features. By way of example, but not limitation, the sensor 206 can sense biological and/or chemical features such as a level of lactate, glucose, cholesterol and/or urea in the body of the wearer of the contact lens 200. In some embodiments, the sensor 206 can sense other features, including, but not limited to, pressure, light, acceleration, temperature and/or strain.

While the description describes one sensor 206, and the drawing for FIG. 2A illustrates the same, in various aspects, the circuit 204 can include more than one sensor. For example, in aspects including multiple sensors, the sensors can be formed in any number of different types of configurations, including, but not limited to, a circular array of sensors and/or sensors disposed along the perimeter of the substrate 202. For example, FIG. 2B illustrates a contact lens 210 having components disposed along a perimeter of the substrate 212. For example, sensors 214, 216, 218, hybrid power component 224, photovoltaic cell 220 and the circuitry 222 are disposed along a perimeter of the substrate 212. Other examples of configurations include semi-circular arrangements, square or rectangular arrangements of components positioned around the periphery of the iris, for example, or the like.

In various aspects, the sensors can be positioned over the surface of the substrate 202 in any number of different configurations. For example, FIG. 2C illustrates a contact lens 230 having sensors 234, 238 disposed across the surface of the substrate 232. As shown, the contact lens 230 can also include a hybrid power component 244, photovoltaic cell 236 and/or circuitry 242 disposed across the surface of the substrate 232. In various aspects, the sensors 234, 238 can be disposed across 25%, 50% or 75% of the surface of the substrate 232. In these aspects, one or more of the sensors 234, 238 can be transparent or translucent in order to enable a wearer of the contact lens 230 to view a sufficient portion of the environment outside of the contact lens 230.

Accordingly, as illustrated in FIGS. 2A, 2B, 2C, different numbers, configurations and/or transparency levels of the sensors and/or other components of the contact lens are envisaged herein and can be implemented according to space and/or design considerations.

Turning back to FIG. 2A, in some aspects, the one or more photovoltaic cells 203, 205 can receive light incident on the photovoltaic cells 203, 205. In various aspects, the light can be sunlight and/or ambient light.

In some aspects, the photovoltaic cells 203, 205 can generate solar power based on the received light. In various aspects, the one or more photovoltaic cells 203, 205 can output solar energy to the hybrid power component 208.

In some aspects, the one or more photovoltaic cells 203, 205 can output solar power to trickle charge a storage capacitor (not shown) of the power storage component 207, to enable a memory (not shown) in the circuit 204 to retain state information and/or to enable the sensor 206 to sense information associated with the wearer of the contact lens 200 (or about an environment outside of the contact lens). For example, in some aspects, the photovoltaic cells 203, 205 can convert the light received into electricity. The electricity can be output at a rate that is approximately equal to the rate of discharge of the electrical charge of the storage capacitor. As such, the rate of electricity output from the photovoltaic cells 203, 205 can be such that the storage capacitor receives a trickle charge. In other embodiments, the power storage component 207 can be or include a thin film battery.

In various aspects, the one or more photovoltaic cells 203, 205 can be disposed across 25%, 50% or 75% of the surface of the substrate 202. In these aspects, one or more of the photovoltaic cells 203, 205 can be transparent or translucent in order to enable a wearer of the contact lens 200 to view a sufficient portion of the environment outside of the contact lens 200.

While the term "photovoltaic cell" has been used herein, in various aspects, solar cells can be employed in lieu of or in addition to the one or more photovoltaic cells 203, 205.

The power storage component 207 can store power from the photovoltaic cells 203, 205. In various aspects, the power storage component 207 can include a storage capacitor (not shown) that can store a charge based on the power stored at the power storage component 207. The stored power can be employed for one or more different functions of the contact lens 200. For example, the stored power can be employed to retain state information in the memory of the circuitry 209. The stored power can be employed to retain state information by maintaining the memory of the circuitry 209 in an on state and/or in a state such that the state information stored in the memory is not erased.

The circuitry 209 can perform one or more functions including, but not limited to, processing information sensed by the sensor 206, communicating with an external reader or other device (e.g., RF reader 114 of FIG. 1), processing information or the like. In some aspects, the circuitry 209 can determine the information (e.g., level of glucose, cholesterol urea or lactate or pressure, light, acceleration, temperature and/or strain) sensed at the sensor 206 and/or output such information.

Figure 3:
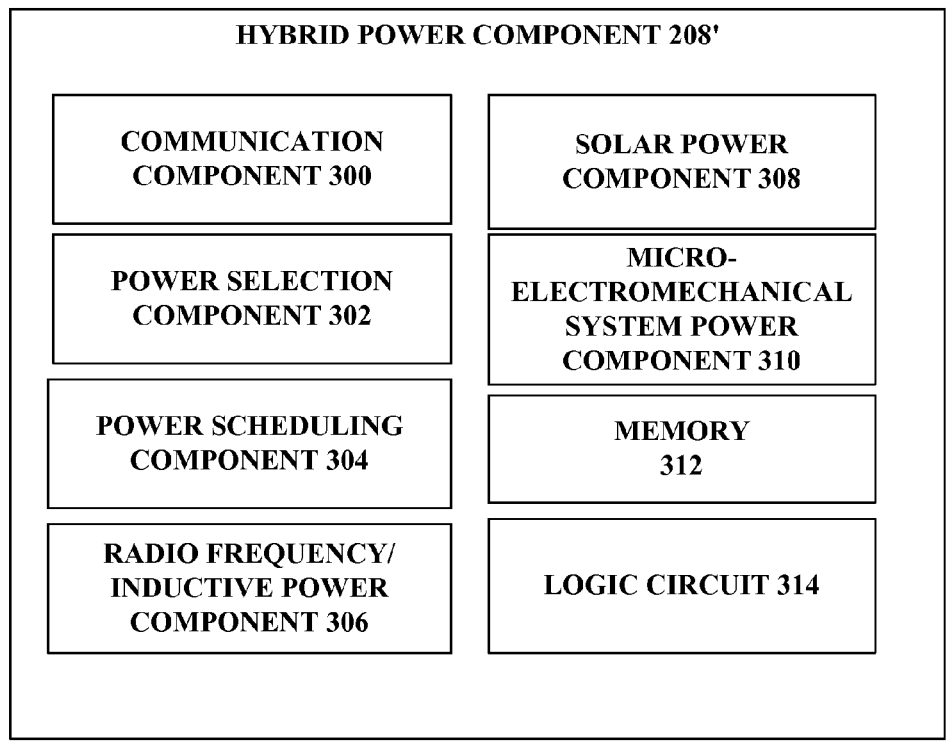
FIG. 3 is an illustration of a block diagram of an exemplary non-limiting hybrid power component that facilitates contact lenses having hybrid power sources in accordance with aspects described herein.

The hybrid power component 208 will be described in detail with reference to FIGS. 2A and 3. FIG. 3 is an illustration of a block diagram of an exemplary non-limiting hybrid power component that facilitates contact lenses having hybrid power sources in accordance with aspects described herein. In various aspects, one or more of the structure and/or functionality described with reference to the hybrid power component 208 can be included in the hybrid power component 208' (and vice versa).

The hybrid power component 208' can be referred to as a hybrid power component because the component can select and/or output different types of power to the circuit of the contact lens in various aspects. It is to be appreciated that respective power sources described herein can be employed to provide power to a storage device (e.g., capacitor) and/or directly provide power to devices or circuitry. Moreover, one or more of the power sources can be employed individually or in cooperation with other power sources (e.g., to provide load balancing, redundancy, fail-over, etc.). The hybrid power component can select optimal power source(s) to employ given state of user, device, environment, etc.

With reference to FIG. 3, the hybrid power component 208' can include a communication component 300, power selection component 302, power scheduling component 304, RF/inductive power component 306, solar power component 308, MEMS power component 310, memory 312 and/or logic circuit 314. In some aspects, one or more of the communication component 300, power selection component 302, power scheduling component 304, RF/inductive power component 306, solar power component 308, MEMS power component 310, memory 312 and/or logic circuit 314 can be electrically and/or communicatively coupled to one another to perform one or more functions of the hybrid power component 208'.

The communication component 300 can transmit and/or receive information. For example, the communication component 300 can transmit information indicative of the features sensed by the sensor 206. As another example, the communication component 300 can receive information or energy from an RF reader, light source or the like.

The power selection component 302 can select a type of power to output from the hybrid power component 208'. For example, the hybrid power component 208' can supply different types of power to the circuitry 209, sensor 206 and/or any other portions of the contact lens 200. In various aspects, the different types of power can include, but are not limited to, RF/inductive power, solar power and/or MEMS-generated electric power.

The RF/inductive power component 306 can receive RF energy from an RF reader in the geographic proximity of the contact lens 200. In some aspects, the RF reader can be the RF reader 114 of FIG. 1. In some aspects, the RF/inductive power component 306 can include an antenna that can receive the RF energy. The RF/inductive power component 306 can employ the received RF energy to generate RF/inductive power in some aspects. The RF/inductive power can be output from the hybrid power component 208 to the sensor 206, circuitry 209 or any of the components of the contact lens 200.

The solar power component 308 can receive solar energy from sunlight and/or ambient light incident on the one or more photovoltaic cells 203, 205 of the contact lens 200. The solar power component 308 can employ the received solar energy to generate solar power in some aspects. The solar power can be output from the hybrid power component 208' to the sensor 206, circuitry 209 or any of the components of the contact lens 200.

The MEMS power component 310 can generate electric power. In some aspects, the MEMS power component 310 can include one or more MEMS devices adapted to generate power based, at least, on the stress and corresponding deformation applied to the contact lens when the wearer of the contact lens 200 blinks. As such, electric power can be output from the hybrid power component 208' to the sensor 206, circuitry 209 or any of the components of the contact lens 200.

The power scheduling component 304 can cause the hybrid power component 208' to output different types of power continually, intermittently, periodically, based upon a condition being satisfied, based on an environment outside of the contact lens 200 and/or based on the operations performed on or via the contact lens 200, as described below in greater detail in the subsequent paragraphs.

For example, in various aspects, the power scheduling component 304 can cause one or more different types of power to be supplied from the hybrid power component 208' concurrently and/or in series. For example, in aspects wherein the different types of power are supplied in series, at a first time, a first type of power can be supplied and at a second time, a second type of power can be supplied. By way of example, but not limitation, RF/inductive power can be output at a first time, solar power can be output at a second time and RF/inductive power can be output again at a third time. The type of power output can be alternated between any number of different types of power. Accordingly, one or more different types of power can be intermittently output in sequence from the hybrid power component 208'.

In some aspects, the power scheduling component 304 can cause the hybrid power component 208' to output the one or more different types of power based on one or more different environmental conditions (e.g., time of day, hour, weather condition indicating whether light is available to power the one or more photovoltaic cells 203, 205 (e.g., level of fog or overcast conditions in the environment)). In various aspects, the time at which particular power is output can be static and/or dynamically-determined.

In some aspects, the power scheduling component 304 can cause the hybrid power component 208' to output the one or more different types of power based on whether a particular source of power is available to the hybrid power component 208'. For example, if a light source is available, the hybrid power component 208' can generate and output solar power. As another example, if an RF reader is available, the hybrid power component can receive RF energy from the RF reader and generate and output RF/inductive power. As another example, if neither solar nor RF energy is available (e.g., the environment is void of light and the contact lens 200 is not near an RF reader), the hybrid power supply can output MEMS-generated electric power.

In some aspects, the power scheduling component 304 can cause the hybrid power component 208' to output the one or more different types of power based on the type of operations performed on or via the contact lens 200 (or sensor 206 or circuitry 209 of the contact lens 200). For example, a first type of operation can require a first level of power and a second type of operation can require a second level of power. The operations can include, but are not limited to, sensing, processing, communication or any of a number of different types of operations performed on or via the circuit 204. The hybrid power component 208' can output a type of power that meets or exceeds the level of power required for the operation to be performed.

In some aspects, the power scheduling component 304 can cause the hybrid power component 208' to output power periodically. For example, the hybrid power component 208' can awake and output power at periodic intervals to enable the contact lens 200 to perform sensing, communication and/or any number of other different types of functions. In some aspects, the hybrid power component 208' can awake at periodic intervals and the circuit 204 can output information indicative of sensed information. The information can be output to the RF reader or the like.

The hybrid power component 208' can include a memory 312 and a logic circuit 314. For example, the memory 312 can be a computer-readable storage medium storing computer-executable instructions and/or information for performing the functions described in this disclosure with reference to the contact lens 200 (or components thereof). The logic circuit 314 can perform one or more of the functions described in this disclosure with reference to the contact lens 200 (or components thereof).

Turning back to FIG. 2A, although not shown, in various aspects, the contact lens 200 can include a memory and/or logic circuit separate from the memory 312 and the logic circuit 314. In various aspects, a single memory and a single logic circuit can be employed on the contact lens 200.

Figure 4:
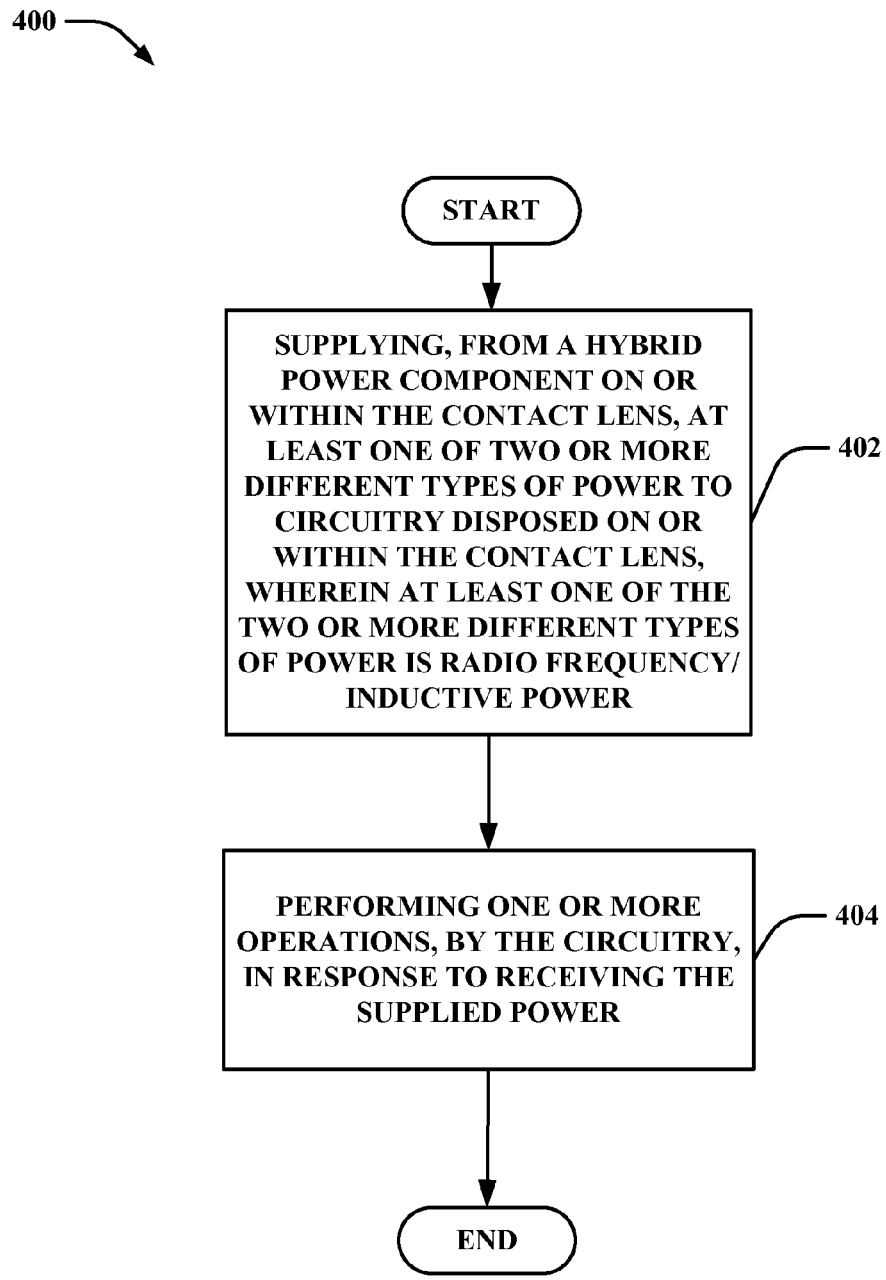
FIGS. 4, 5 and 6 are illustrations of exemplary flow diagrams of methods that facilitate contact lenses having hybrid power sources in accordance with aspects described herein.
Figure 5:
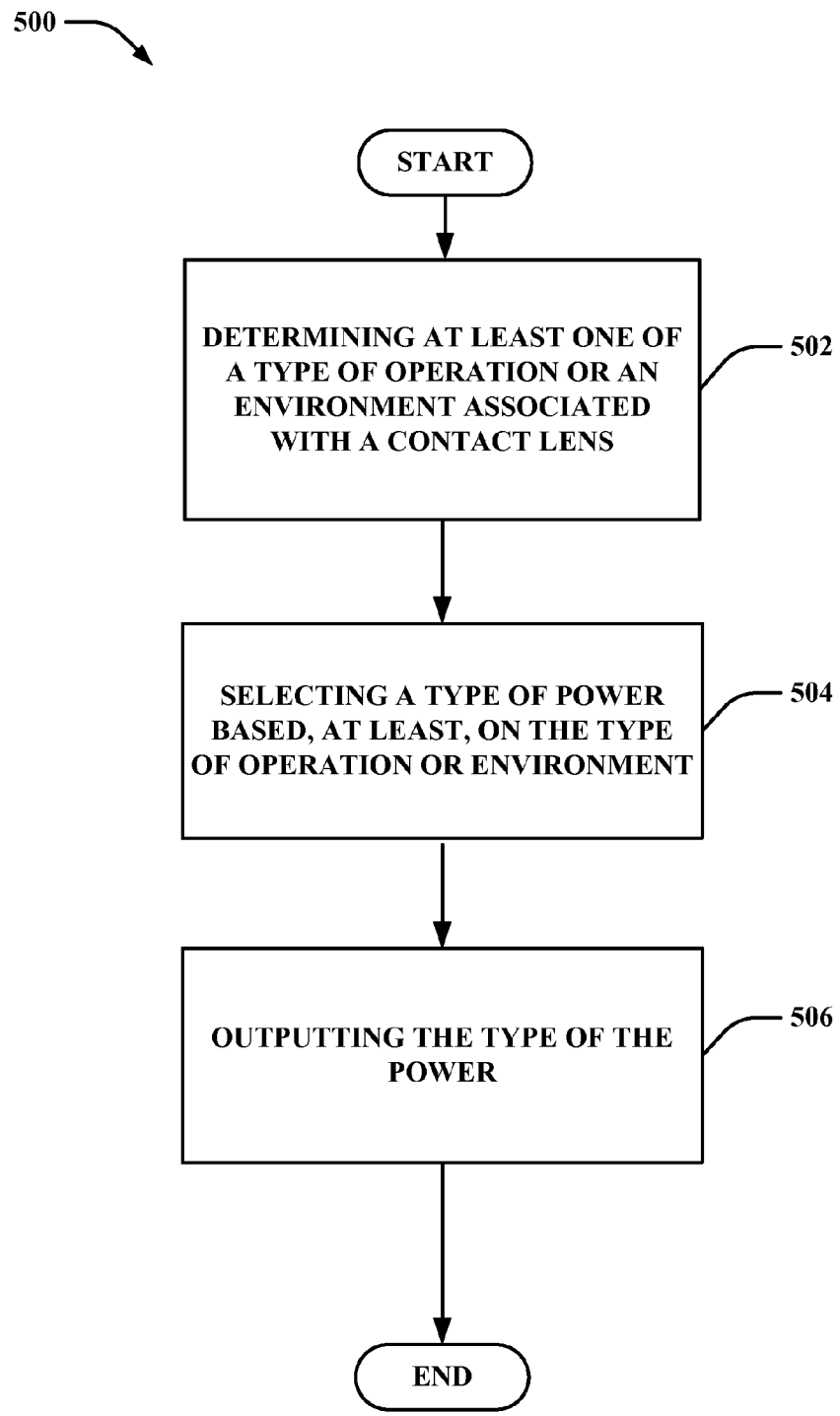
Figure 6:
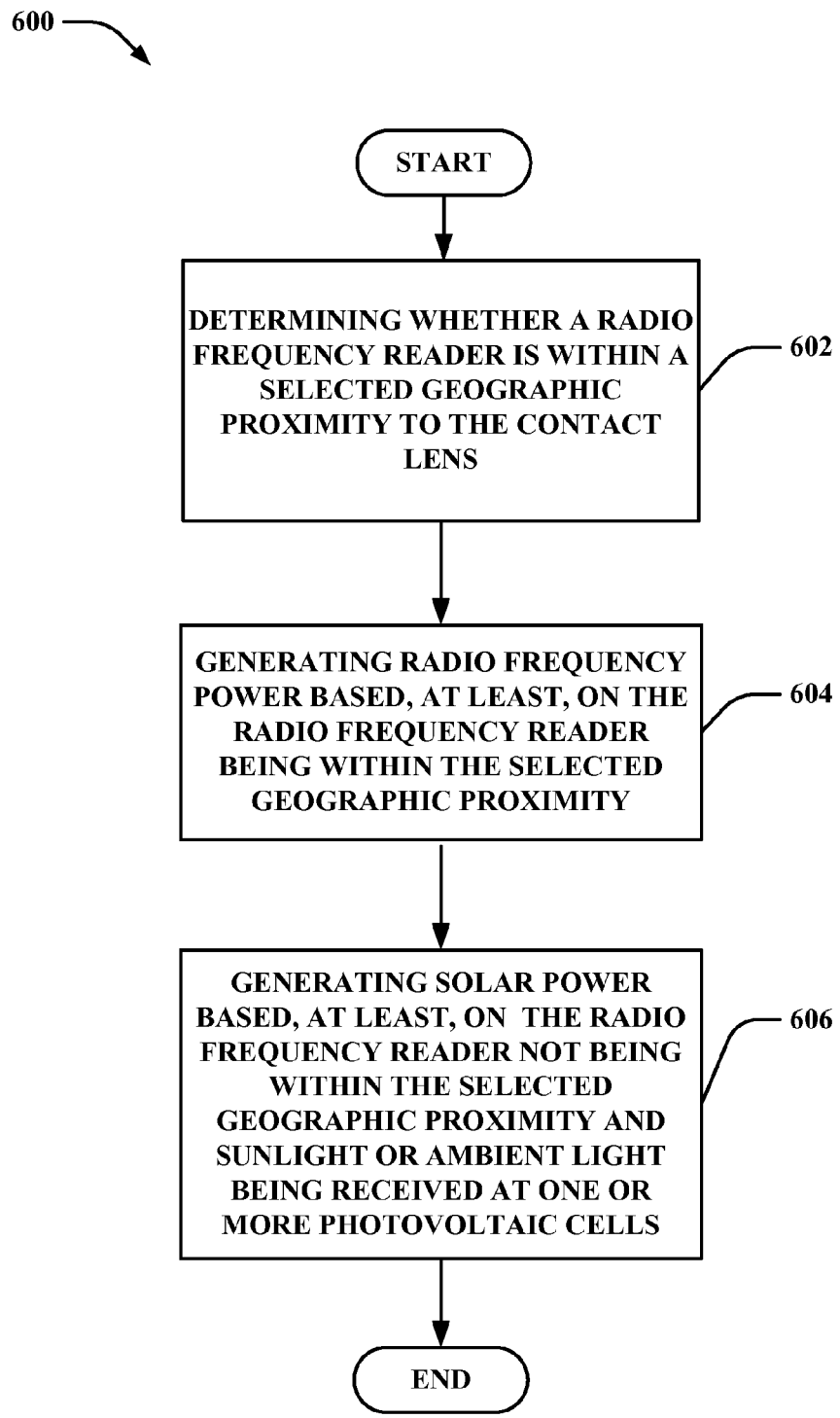

FIGS. 4, 5 and 6 are illustrations of exemplary flow diagrams of methods that facilitate contact lenses having hybrid power sources in accordance with aspects described herein. Turning first to FIG. 4, at 402, method 400 can include supplying, from a hybrid power component on or within the contact lens, at least one of two or more different types of power to circuitry disposed on or within the contact lens, wherein at least one of the two or more different types of power is RF/inductive power (e.g., using the hybrid power component 208'). In some aspects, two or more different types of power can be supplied to the circuitry. For example, solar, RF and/or MEMS-based power can be supplied to the circuitry.

In some aspects, the power can be supplied intermittently. For example, at a first time, a first type of power can be supplied and at a second time, a second type of power can be supplied.

The time at which a particular type of power is output can be static and/or dynamically-determined based on any number of factors including, but not limited to, the environment of the contact lens wearer. For example, in various aspects, the type of power supplied can be based on whether a particular source of power is available to the hybrid power component. For example, if a light source is available, the hybrid power component can output solar power. As another example, if an RF reader is available, the hybrid power component can receive RF energy from the RF reader and output RF/inductive power. As another example, if neither solar nor RF energy is available (e.g., the environment is void of light and is not near an RF reader), the hybrid power supply can output MEMS-generated electric power.

In some aspects, the type of power supplied can be based on the operations performed by the circuitry. For example, a first type of operation can require a first level of power and a second type of operation can require a second level of power. The hybrid power component can output a type of power that meets or exceeds the power required for the operation.

At 404, method 400 can include performing one or more operations, by the circuitry, in response to receiving the supplied power (e.g., using the circuit 204). By way of example, but not limitation, the operations can include sensing, processing, communication or any of a number of different types of operations performed on or via the circuit 204.

Turning now to FIG. 5, at 502, method 500 can include determining at least one of a type of operation or an environment associated with the contact lens (e.g., using the hybrid power component 208'). In some aspects, the environment can be a time of day (e.g., nighttime, twilight, daytime or hour), an indicator of whether light is available to power photovoltaic cells (e.g., level of fog or overcast conditions in the environment), whether an RF reader is within a particular geographic proximity to the circuit 204 or the like. In aspects, the operation type can include, but is not limited to, sensing, communication or the like.

At 504, method 500 can include selecting a type of power based, at least, on the type of the operation or environment (e.g., using the hybrid power component 208'). For example, the type of power can be RF, solar and/or MEMS-generated power and can be determined based on whether sensing is being performed, for example. As another example, the type of power can be based on whether nighttime conditions exist, for example, and solar power is not available.

At 506, method 500 can include outputting the type of the power (e.g., using the hybrid power component 208'). In various aspects, the power can be output continually and/or intermittently.

As one example, in some aspects, two or more different types of power can be intermittently output in sequence from the hybrid power component. By way of example, but not limitation, RF/inductive power can be output at a first time, solar power can be output at a second time and RF/inductive power can be output again at a third time. The type of power output can be alternated between any number of different types of power.

In another example, power can be output periodically. In another example, power of a first type can be output during a time period corresponding to a first type of operation or environmental condition while power of a second type can be output during a time period corresponding to a second type of operation or environmental condition.

Turning now to FIG. 6, at 602, method 600 can include determining whether a RF reader is within a selected geographic proximity to the contact lens (e.g., using the communication component 300).

At 604, method 600 can include generating RF/inductive power based, at least, on the RF reader being within the selected geographic proximity (e.g., using the hybrid power component 208'). For example, the RF/inductive power can be generated upon receiving a signal from the RF reader.

At 606, method 600 can include generating solar power based, at least, on the RF reader not being within the selected geographic proximity and sunlight or ambient light being received at one or more photovoltaic cells (e.g., using the hybrid power component 208').

Exemplary Networked and Distributed Environments

Figure 7:
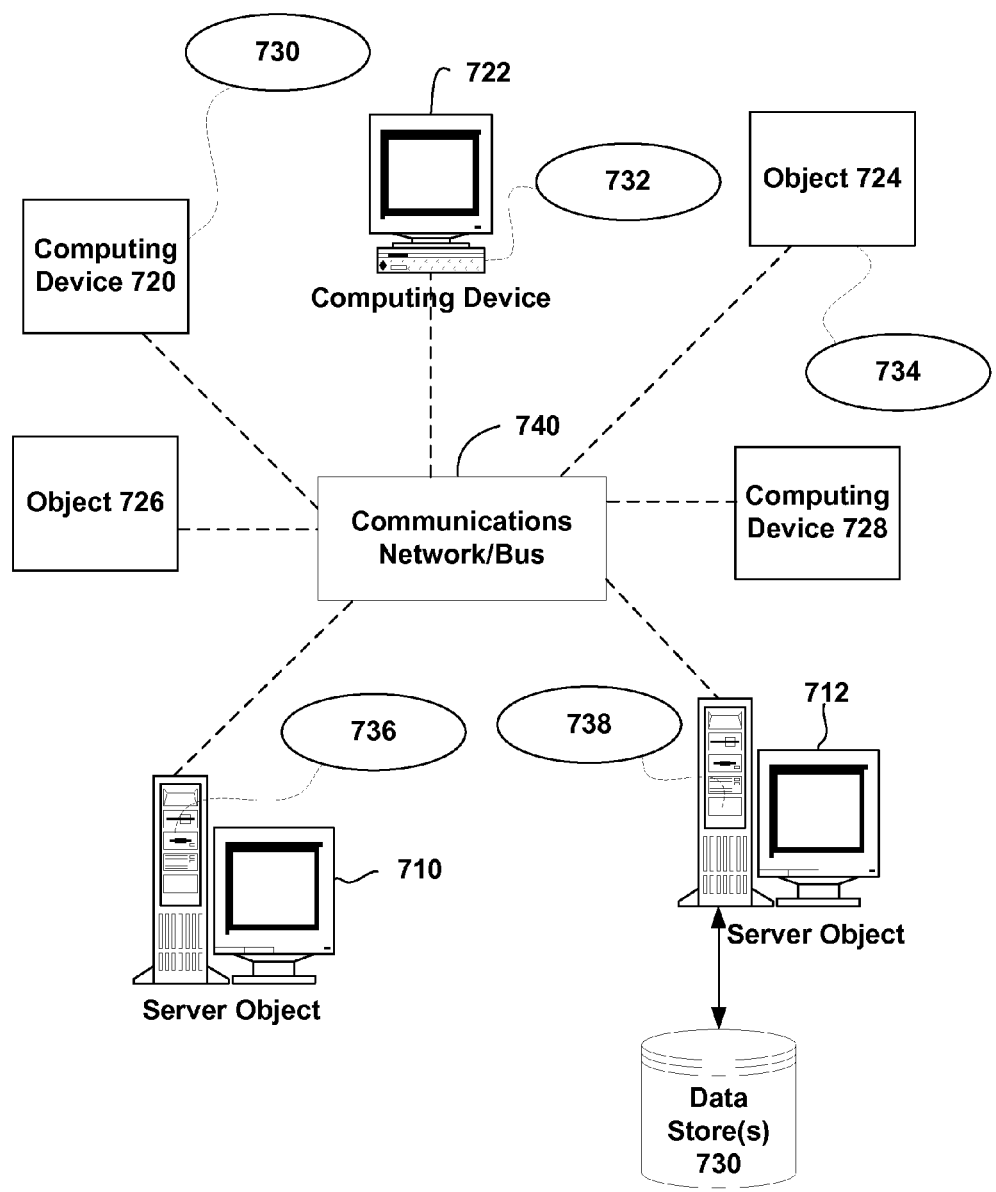
FIG. 7 is an illustration of a schematic diagram of an exemplary networked or distributed computing environment for implementing one or more aspects described herein.

FIG. 7 provides a schematic diagram of an exemplary networked or distributed computing environment with which one or more aspects described in this disclosure can be associated. The distributed computing environment includes computing objects 710, 712, etc. and computing objects or devices 720, 722, 724, 726, 728, etc., which can include programs, methods, data stores, programmable logic, etc., as represented by applications 730, 732, 734, 736, 738. It can be appreciated that computing objects 710, 712, etc. and computing objects or devices 720, 722, 724, 726, 728, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 710, 712, etc. and computing objects or devices 720, 722, 724, 726, 728, etc. can communicate with one or more other computing objects 710, 712, etc. and computing objects or devices 720, 722, 724, 726, 728, etc. by way of the communications network 740, either directly or indirectly. Even though illustrated as a single element in FIG. 7, network 740 can include other computing objects and computing devices that provide services to the system of FIG. 7, and/or can represent multiple interconnected networks, which are not shown.

In a network environment in which the communications network/bus 740 can be the Internet, the computing objects 710, 712, etc. can be Web servers, file servers, media servers, etc. with which the client computing objects or devices 720, 722, 724, 726, 728, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens) and/or reader described herein. In various aspects, the data store can include or be included within, any of the memory described herein, any of the contact lenses described herein and/or the RF reader described herein. In various aspects, the data store can be any repository for storing information transmitted to or received from the contact lens.

Figure 8:
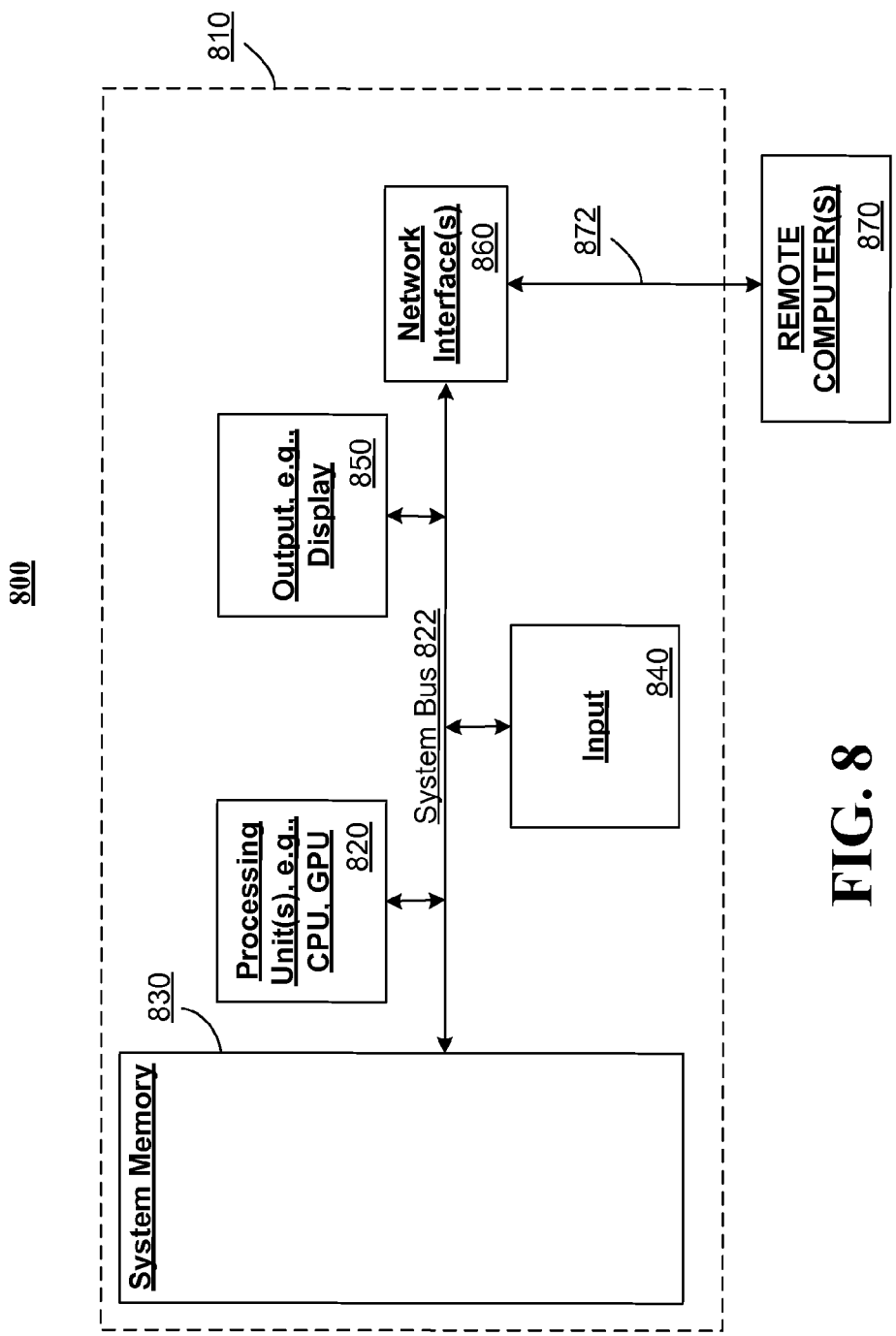
FIG. 8 is an illustration of a schematic diagram of an exemplary computing environment for implementing one or more aspects described herein.

FIG. 8 illustrates an example of a suitable computing system environment 800 in which one or aspects of the aspects described in this disclosure can be implemented. Components of computer 810 can include, but are not limited to, a processing unit 820, a system memory 830, and a system bus 822 that couples various system components including the system memory to the processing unit 820.

Computer 810 typically includes a variety of computer readable media and can be any available media that can be accessed by computer 810. The system memory 830 can include computer storage media in the form of volatile and/or nonvolatile memory such as read only memory (ROM) and/or random access memory (RAM). By way of example, and not limitation, memory 830 can also include an operating system, application programs, other program components, and program data.

A user can enter commands and information into the computer 810 through input devices 840 (e.g., keyboard, keypad, a pointing device, a mouse, stylus, touchpad, touch screen, motion detector, camera, microphone or any other device that allows the user to interact with the computer 810). A monitor or other type of display device can be also connected to the system bus 822 via an interface, such as output interface 850. In addition to a monitor, computers can also include other peripheral output devices such as speakers and a printer, which can be connected through output interface 850.

The computer 810 can operate in a networked or distributed environment using logical connections to one or more other remote computers, such as remote computer 880. The remote computer 880 can be a personal computer, a server, a router, a network PC, a peer device or other common network node, or any other remote media consumption or transmission device, and can include any or all of the elements described above relative to the computer 810. The logical connections depicted in FIG. 8 include a network 882, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and nonvolatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A sensing device for a body, comprising:
a substrate; and
a circuit comprising:
one or more sensors disposed on or within the substrate, wherein the one or more sensors are configured to sense a level of at least one of lactate, glucose, cholesterol or urea in the body;
circuitry disposed on or within at least a portion of the substrate;
one or more photovoltaic cells disposed on or within at least a portion of the substrate; and
a hybrid power component disposed on or within the substrate, wherein the hybrid power component selects at least one of two or more different types of power based on at least an operation of the circuitry or an environment of the sensing device and supplies the selected at least one of two or more different types of power to the circuitry, wherein one of the two or more different types of power is photovoltaic power provided by the one or more photovoltaic cells.

2. The sensing device of claim 1, wherein another one of the two or more different types of power is radio frequency/inductive power.

3. The sensing device of claim 2, wherein the hybrid power component supplies the radio frequency/inductive power and the photovoltaic power intermittently.

4. The sensing device of claim 1, further comprising one or more microelectromechanical systems and wherein another one of the two or more different types of power is electric power provided by the one or more microelectromechanical systems.

5. The sensing device of claim 4, wherein the hybrid power component supplies the photovoltaic power and the electric power from the one or more microelectromechanical systems intermittently.

6. The sensing device of claim 1, further comprising a power storage component, wherein the power storage component is operably coupled to the one or more photovoltaic cells, and wherein the power storage component is configured to store power from the one or more photovoltaic cells.

7. The sensing device of claim 6, wherein the power storage component comprises a storage capacitor.

8. The sensing device of claim 6, wherein the power storage component comprises a thin film battery.

9. The sensing device of claim 1, wherein the one or more photovoltaic cells are translucent or transparent.

10. The sensing device of claim 9, wherein the one or more photovoltaic cells are disposed over at least half of a surface of the substrate.

11. The sensing device of claim 1, wherein at least one of the one or more photovoltaic cells or the circuitry is disposed along a perimeter of the substrate.

12. The sensing device of claim 1, wherein the one or more photovoltaic cells comprise a circular array of two or more photovoltaic cells.

13. The sensing device of claim 1, wherein the hybrid power component supplies at least two of the two or more different types of power to the circuitry and alternates between supplying a first one of the at least two of the two or more different types of power and supplying a second one of the at least two of the two or more different types of power.

14. The sensing device of claim 1, wherein the sensing device is a wearable device.

15. The sensing device of claim 1, wherein the sensing device is a contact lens.

16. A contact lens, comprising:
a substrate; and
a circuit comprising:
one or more sensors disposed on or within the substrate;
circuitry disposed on or within at least a portion of the substrate; and
a hybrid power component configured to select at least one of two or more different types of power, wherein the hybrid power component is further configured to output the selected at least one of two or more different types of power to the circuitry, wherein at least one of the two or more different types of power is radio frequency/inductive power.

17. The contact lens of claim 16, further comprising a power storage component, wherein the power storage component is operably coupled to a power source of at least one of the two or more different types of power, and wherein the power storage component is configured to store power from the power source.

18. The contact lens of claim 17, wherein the power storage component comprises a storage capacitor.

19. The contact lens of claim 17, wherein the power storage component comprises a thin film battery.

20. The contact lens of claim 16, further comprising one or more photovoltaic cells disposed on or within at least a portion of the substrate, wherein another one of the two or more different types of power is photovoltaic power provided by the one or more photovoltaic cells.

21. The contact lens of claim 16, wherein the one or more sensors sense a level of at least one of lactate, glucose, cholesterol or urea in a body of a wearer of the contact lens.

22. The contact lens of claim 16, wherein the one or more sensors sense at least one of pressure, light, acceleration, temperature or strain.

23. The contact lens of claim 16, further comprising one or more microelectromechanical systems and wherein another one of the two or more different types of power is electric power provided by the one or more microelectromechanical systems.

24. The contact lens of claim 16, wherein the hybrid power component supplies a type of power based, at least, on an operation of the circuitry or an environment of the contact lens.

25. The contact lens of claim 16, wherein the hybrid power component supplies at least two of the two or more different types of power to the circuitry and alternates between supplying a first one of the at least two of the two or more different types of power and supplying a second one of the at least two of the two or more different types of power.

26. A method of operating a contact lens, comprising:
selecting at least one of two or more different types of power, wherein at least one of the two or more different types of power is radio frequency/inductive power;
supplying, from a hybrid power component, the selected at least one type of power to circuitry disposed on or within the contact lens; and
performing one or more operations, by the circuitry, in response to receiving supplied power.

27. The method of claim 26, wherein the selecting comprises selecting two or more different types of power.

28. The method of claim 27, wherein the two or more different types of power comprise radio frequency/inductive power and photovoltaic power.

29. The method of claim 27, wherein the two or more different types of power comprise radio frequency/inductive power and electric power from a microelectromechanical system.

30. The method of claim 27, wherein the two or more different types of power are supplied at based, at least, on an environment outside of the contact lens.

31. The method of claim 27, wherein supplying the selected at least one type of power comprises supplying the radio frequency/inductive power during a first type of operation performed by the circuitry and supplying a second type of power during a second type of operation performed by the circuitry.

32. A method of operating a contact lens, comprising:
determining at least one of a type of operation performed via the contact lens or an environment outside of the contact lens;
selecting at least one of two or more different types of power based, at least, on the determined type of operation or the determined environment outside of the contact lens; and
outputting the selected at least one of two or more different types of power from a hybrid power component of the contact lens.

33. The method of claim 32, wherein determining at least one of a type of operation performed via the contact lens or an environment outside of the contact lens comprises determining whether the environment outside of the contact lens is a nighttime environment.

* * * * *